US006407299B1

(12) United States Patent
Sen et al.

(10) Patent No.: US 6,407,299 B1
(45) Date of Patent: Jun. 18, 2002

(54) ALKYL MAGNESIUM CATALYZED SYNTHESIS OF ETHYLENE AND α-OLEFIN POLYMERS

(75) Inventors: Ayusman Sen; Jang Sub Kim, both of State College, PA (US)

(73) Assignees: ExxonMobile Research and Engineering Company, Annandale, NJ (US); The Pennsylvania State Research Foundation, University Park, PA (US)

(*) Notice: Subject to any disclaimer, the term of this patent is extended or adjusted under 35 U.S.C. 154(b) by 0 days.

(21) Appl. No.: 09/586,091

(22) Filed: Jun. 2, 2000

Related U.S. Application Data

(60) Provisional application No. 60/137,199, filed on Jun. 2, 1999.

(51) Int. Cl.[7] ............. C10M 107/04; C08F 10/00; C07C 2/34
(52) U.S. Cl. ............. 585/10; 585/18; 585/511; 585/525; 502/169; 502/202; 502/226
(58) Field of Search ............. 585/10, 18, 525, 585/511; 502/169, 202, 226

(56) References Cited

U.S. PATENT DOCUMENTS

| 3,737,393 A |   | 6/1973  | Vries ................... 252/431 |
|-------------|---|---------|----------------------------------|
| 4,510,342 A | * | 4/1985  | Currie et al. ........... 585/524 |
| 4,657,882 A | * | 8/1987  | Karayannis et al. ..... 526/125   |
| 4,704,491 A | * | 11/1987 | Tsutsui et al. ......... 585/10   |
| 5,504,166 A | * | 4/1996  | Buchelli et al. ........ 526/60   |
| 5,561,095 A |   | 10/1996 | Chen et al. ........... 502/169   |
| 5,648,580 A | * | 7/1997  | Chen et al. ........... 585/462   |
| 5,880,241 A |   | 3/1999  | Brookhart et al. ..... 526/348    |
| 6,060,633 A | * | 5/2000  | Chen et al. ........... 585/475   |

FOREIGN PATENT DOCUMENTS

| EP | 0003716   | 8/1979 | ....... C08F/10/00 |
| EP | 0262947   | 4/1988 | ....... C01B/3/38  |
| WO | WO9919249 | 4/1999 | ....... C01B/3/00  |

OTHER PUBLICATIONS

"Hydrogen Generation From Natural Gas for the Fuel Cell Systems of Tomorrow", Andrew L. Dicks; British Gas plc., Gas Research Center, Ashby Road, Loughborough, Leic. LE11 3Qu, U.K.; Journal of Power Sources, CH, Elsevier Sequoia S. A. Lausanne; vol. 61, No. 1–2, Jul. 8, 1986, pp. 113–124.

\* cited by examiner

*Primary Examiner*—Jacqueline V. Howard
(74) *Attorney, Agent, or Firm*—Kenneth W. Peist; Joseph C. Wang

(57) ABSTRACT

The present invention is a two-component catalyst system comprising (a) an alkyl magnesium ($MgR_2$) component and (b) a Lewis acid component. The catalyst system is used for catalyzing the oligomerization and polymerization of ethylene and/or α-olefins to form homopolymers and copolymers. The products range from highly linear, high molecular weight, solid polymers to highly branched, lower molecular weight oils.

17 Claims, No Drawings

ALKYL MAGNESIUM CATALYZED SYNTHESIS OF ETHYLENE AND α-OLEFIN POLYMERS

This application claims the benefit of U.S. Provisional Application No. 60/137,199 filed on Jun. 2, 1999.

FIELD OF THE INVENTION

The present invention relates to the oligomerization and polymerization of ethylene and α-olefins using a two part catalyst system comprising an alkyl magnesium component and a Lewis acid. The products range from highly linear, high molecular weight, solid polymers to highly branched, lower molecular weight oils.

BACKGROUND OF THE INVENTION

The polymerization of ethylene, propylene and other α-olefins catalyzed by transition metal catalyst systems has been practiced commercially for many years. For example homo- and copolymers of ethylene with other materials such as olefins (acyclic and/or cyclic, optionally substituted), and other types of monomers, are being used as plastics for packaging materials, molded items, films, etc., and as elastomers for molded goods, belts of various types, in tires, adhesives, and for other uses. It is well known in the art that the structure of these various polymers, and hence their properties and uses, are highly dependent on the catalyst and specific conditions used during their synthesis. In addition to these factors, processes in which these types of polymers can be made at reduced cost are also important. Therefore, improved processes and catalyst systems for making such polymers are of great commercial interest.

Catalysts used in polyolefin preparation can be classified into a limited number of types. Ziegler-Natta type catalysts for polymerization of unsaturated hydrocarbons, such as α-olefins, have long been the state of the art catalysts for such reactions. Typically, Ziegler-Natta type catalysts are composed of transition metal salts and aluminum alkyl compounds. While these catalysts are very effective and have a long-established record of use, they are not without drawbacks. For example, transition metals are expensive, potentially present some toxicity hazards, and to some extent are environmentally objectionable. Therefore, continuing efforts towards development of other suitable olefin polymerization catalysts have occurred. For example, metallocene catalysts have been developed for use in α-olefin polymerizations. Even more recently, there have been attempts to use non-transition metal catalysts like Al compounds. For example, there are cationic Al compounds disclosed in U.S. Pat. No. 5,777,120 and neutral Al compounds disclosed by Sen et al. (Polym. Prepr. 34 (2) 818 (1998)). However, until the present invention, combinations of non-transition metal catalysts (e.g. Mg and Al) for these purposes were unknown.

The polymerization of ethylene and α-olefins typically leads to the formation of highly linear polymers. One use for these polymers, when in a fluid form, is for synthetic lubricant compositions. However, polymerization of ethylene, the most widely available and least expensive of the olefins, by transition metal catalysts usually leads to the formation of solid polymers. Thus polyethylene is commonly used to make plastic containers such as milk jugs and for plastic films. As such, polyethylene is generally not suitable for use as soft materials or lubricants for most applications. Thus significant research continues to be performed to discover improved methods for synthesizing liquid polyolefins, especially polyethylene.

In general, synthetic lubricants are more desirable as they tend to provide lower friction and increased mechanical efficiency across the full spectrum of mechanical loads and do so over a wider range of operating conditions relative to traditional oil lubricants. The objective of industrial research on synthetic lubricants is, in general, to achieve a polymeric fluid that exhibits a useful viscosity over a wide range of temperature, i.e., has a good viscosity index (VI), while also exhibiting good lubricity, and a pour point equal to or better than mineral oil. One characteristic of the molecular structure of the polymeric fluids has been found to correlate very well with all of these desirable lubricant properties. This characteristic is the polymer's branching index, BI. BI is the ratio of methyl protons to total non-aromatic, aliphatic group protons in the polymer product. The BI of a polymer is easily determined from proton NMR spectra by calculating the ratio of non-aromatic methyl hydrogens centered around 0.85 ppm, to the total non-aromatic aliphatic hydrogens in the range of 0.5 to 2.1 ppm. BI is related to the number of branches (n) per 1000 methylene ($CH_2$) groups in the following way: BI=3n/2000.

Generally, as the BI increases, the pour point of the polymer fluid, i.e., the temperature at which the composition changes from a liquid to a solid, decreases. This is a desirable effect as a lower pour point extends the application range of the polymer fluid. BI, however, has a negative effect on the viscosity index of a polyethylene oil; it is well-known in the art that the viscosity index of polyethylene fluids decreases as the branching index increases. This is an undesirable effect because a lower viscosity index indicates a poor viscosity-temperature performance. Thus, the challenge in synthesizing polyethylene fluids is to achieve an amount of branching sufficient to maintain the polyethylene in a liquid state such that the polyethylene fluid has a good viscosity index.

Recently there have been a number of discoveries in the synthesis of branched polyethylene polymers. For example, DuPont and the University of North Carolina, have developed novel Ni(II) and Pd(II) based catalysts which catalyze the polymerization of ethylene to form polyethylene liquids. In this PCT Application (No. WO 96/23010) it has been disclosed that polymers having a moderate degree of branching can be synthesized by using palladium and nickel catalysts incorporating very bulky chelating α-diimine bidentate ligands. The PCT application discloses, for example, polyolefins having about 80 to about 150 branches per 1000 methylene groups, wherein for every 100 branches that are methyl branches, there are about 30 to about 90 ethyl branches, about 4 to about 20 propyl branches, about 15 to about 50 butyl branches, about 3 to about 15 amyl branches, and about 30 to about 140 hexyl or longer branches. The olefin polymers described in the PCT application are said to be usefull as elastomers, molding resins, in adhesives, etc. Polymers containing monomer units derived other than from olefins are also disclosed in the PCT application; and polymers which contain olefin and olefinic ester monomer units, particularly copolymers of ethylene and methyl methacrylate and/or other acrylic esters, are said to be useful as viscosity modifiers for lubricating oils. The basis for the above PCT Application is believed to be an article by Johnson et al published in the Journal of the American Chemical Society (*New Pd(II)and Ni(II)-Based Catalysts for Polymerization of Ethylene and α-Olefins*, J. Am. Chem. Soc. 1995, 117, 6414–6415). In these systems, however, the degree of branching is only 20 to 150 branches per 1,000 $CH_2$ groups.

Other highly active Nickel(II) and Palladium(II)-based catalysts have been discovered by researchers at The Pennsylvania State University and have been employed for the preparation of highly branched polyethylene fluids having greater than 587 branches per 1000 $CH_2$ groups. These polymers and their synthesis have been reported by J. S. Kim, J. H. Powlow, L. M. Wojcinski, S. Murtuza, S. Kacker, and A. Sen, "*Novel Nickel(II) and Palladium(II)-Based Catalyst Systems for the Synthesis of Hyperbranched Polymers from Ethene*", J. Am. Chem. Soc. 120, 1932, 1998. Such highly branched polymers, however, have a VI that typically is too low to be used as, for example, a lube basestock. See also WO 98/33823 titled "Metal Catalyzed Synthesis of Hyperbranched Ethylene and/or α-olefin Polymers".

Another recent international patent application (PCT Application No. WO 97/02298) relates to the preparation of polyolefins by coordination polymerization of ethylene, styrene or norbornene using a catalyst comprising (a) a zerovalent tricoordinate or tetracoordinate nickel compound which has at least one labile ligand, (b) an acid of the formula HX, where X is a noncoordinating anion, and (c) at least one bulky ligand selected from a specified group thereof. At page 29, lines 25 et seq. of that PCT Application, it is suggested that the following materials (among others) should be absent during the polymerization process, or at least should not be present in an amount sufficient to affect the course of the polymerization: an organoaluminum compound; an aluminum halide; and any organometallic compound except for the nickel compounds. The polymers prepared in accordance with that PCT Application are moderately branched and are said to be useful as molding resins, films and elastomers.

A report from Switzerland [Adv. Poly. Sci. 1974,15,1] describes the use of a $TiCl_4/EtAlCl_2$ catalyst for the polymerization of ethylene in benzene to give branched polymers. The products obtained, however, were of relatively low branching and molecular weight. One detrimental side reaction associated with the use of benzene solvent is Friedel-Crafts alkylation of the solvent and thus, a large portion of the product is reported to contain aromatic rings.

Moderately branched ethylene polymers are also disclosed by de Souza et al in an article published in September 1997 ([η3-*methallyl-nickel-dad*] $PF_6$ *Complex: New Catalyst Precursor For Ethylene Polymerization*, Macromol. Rapid Commun., 1997, 18, 795–800). In that article, it is disclosed that [$η^3$-methallylnickel-dad] $PF_6$ is active as an ethylene polymerization catalyst when used in the presence of usual organoaluminum compounds such as diethylaluminum chloride, at low Al/Ni ratios and under mild reaction conditions.

While the hydrocarbon polymers prepared in accordance with the above-discussed PCT applications and articles are characterized by a moderate degree of branching, there remains a need for hyperbranched, viscous, liquid hydrocarbon polymers and to a method for their preparation from simple and inexpensive olefins such as ethylene and propylene. Further, there is a continuing need in the art for polyolefin fluids having a molecular weight, a branching index, and a viscosity index such that they are suitable for use as synthetic lubricants. The present discovery of a novel method of manufacturing solid and liquid polyolefins using non-transition metal catalysts addresses these needs and others.

SUMMARY OF THE INVENTION

It is an object of this invention to provide a novel catalyst system useful for oligomerization, homopolymerization and copolymerization of ethylene and/or α-olefins.

It is also an object of this invention to provide a novel method of making highly linear, high molecular weight, solid polyolefins with a molecular weight of from about 30,000 up to about 2,500,000.

It is an additional object of this invention to provide a novel method of making branched, viscous oils with a molecular weight in the range of from about 300 to about 30,000.

Yet another object is to prepare viscous, oily, branched hydrocarbon compositions that are useful as lubricants and lubricant components by homopolymerizing or copolymerizing α-olefins in the presence of a non-transition metal containing catalyst.

Yet another object of the invention is to supply a catalyst system that produces little or no discoloration in the polymerization product thus eliminating or reducing an extra, costly clean-up step.

These and other objects and advantages are accomplished by the present invention, which comprises a novel catalyst system containing (a) an alkyl magnesium component and (b) a Lewis acid component. The invention also includes the use of the catalyst system for the oligomerization, homopolymerization and copolymerization of α-olefins to form homopolymers and copolymers thereof. Preferably, the reactions are performed in the presence of a solvent and/or reaction promoters.

DETAILED DESCRIPTION OF THE INVENTION

The present invention comprises a catalyst system for the oligomerization or polymerization of ethylene and/or α-olefins to prepare homopolymers or copolymers thereof. The catalyst system contains two components: (a) an alkyl magnesium compound having the formula $MgR_2$ wherein R can be any aliphatic group and (b) a Lewis acid component such as $FeCl_3$ or $AlCl_3$. The reactions are preferably done in the presence of a halogenated or non-halogenated hydrocarbon solvent. The molar ratio of component a:b is in the range of 10:1 to 1:100, preferably about 2:1 to 1:10, and most preferably about 1:1 to 1:6.

In a preferred embodiment for making highly linear, high molecular weight solid polymers the Lewis acid is present at 1 molar equivalent or less. The molecular weight range for these linear solid polymers is generally in the range of about 30,000 up to about 2,500,000; preferably in the range of 50,000–1,500,000 and most preferably they are in the range of about 100,000–1,000,000.

In a preferred embodiment for making branched viscous oils, a Lewis acid is added to the reaction mixture in an amount greater than 1 molar equivalent relative to the alkyl magnesium component. Preferably it is added in an amount of about 2 to about 10 molar equivalent and most preferably in the range of 3–6 molar equivalent. The molecular weight of the viscous oils are generally in the range of from about 300 to about 30,000; preferably they are within the range of about 500 to about 10,000; and most preferably they are within the range of about 700 to about 3,000. This preferred embodiment may be used as a synthetic lubricant basestock. It should be appreciated by those skilled in the art that the term "basestock", as used herein, refers to a hydrocarbon oil without additives or, in the alternative, the primary component in a lubricant formulation.

In yet another preferred embodiment, the synthetic lubricant basestock may be combined with additional lubricating oil additives including, but not limited to, antioxidants, anti-wear additives, extreme pressure antioxidants, anti-wear additives, high pressure additives, friction modifiers, viscosity index improvers, pour point depressants, detergents, dispersants, corrosion inhibitors, metal deactivators, seal compatibility additives, demulsifiers, antifoam additives, and mixtures thereof.

In a preferred aspect of the invention, linear solid polymers and branched viscous liquid polymers are prepared from ethylene as the sole monomer. In other aspects, ethylene may be replaced with or used in combination with other olefins such as propylene, butene, 1-pentene, 1-hexene, 1-dodecene and the like.

The polymerization preferably is carried out in the liquid phase using a halogenated or non-halogenated hydrocarbon solvent. In general any solvent known to those skilled in the art of olefin polymerization can be used. If a solvent is employed, it is preferred that the solvent is either a halogenated compound (preferably aromatic), an aliphatic hydrocarbon comprising from about 5 to about 20 carbons, or a mixture thereof. Examples of halogenated solvents are chlorobenzene, methylene chloride ($CH_2Cl_2$), tetrachloroethane ($C_2H_2Cl_4$), dichlorobenzene ($C_6H_4Cl_2$), trichlorobenzene, bromobenzene, dibromobenzene, tribromobenzene, and alkylated halobenzenes having C1–C10 alkyl groups, such as, for example, p-chlorotoluene, and the like. Especially preferred halogenated solvents are chlorobenzene and dichlorobenzene. Examples of aliphatic hydrocarbon solvents comprising from about 5 to about 20 carbons are toluene, xylenes, pentane, hexane, heptane, decane, and dodecane. These are non-limiting examples however and any halogenated or non-halogenated hydrocarbon solvent that effectively assists the polymerization is acceptable.

The catalyst system of the present invention comprises two components (a) an alkyl magnesium and (b) a Lewis acid. The alkyl magnesium component of the present invention is defined as $MgR_2$ where R is any hydrocarbyl group attached to the magnesium. Suitable R groups include lower alkyls (e.g. methyl, ethyl, propyl, isopropyl, butyl, isobutyl, pentyl, etc.) and cyclic alkyls (e.g. cyclopentyl, cyclohexyl, etc.). Other suitable R groups are aryls and fluorinated alkyls and aryls. Mixtures of the above can also be used. Preferred alkyl magnesium compounds are diethylmagnesium [$Mg(C_2H_5)_2$], dibutylmagnesium [$Mg(C_4H_9)_2$] and dineopentyl-magnesium [$Mg(Np)_2$].

The second component of the catalyst system is a Lewis acid. The Lewis acid component of the present catalyst system may be any Lewis acid known to those skilled in the art. Some non-limiting examples of Lewis acids suitable for use in the present invention include the following: $B(C_6F_5)_3$, $B(C_6H_5)_3$, $BF_3$, $AlR_nX_{3-n}$ (R=alkyl, X=$C_6F_5$, F, Cl Br, n=0–2), $PF_5$, and alkylaluminoxanes. Mixtures of the above can also be used. The preferred Lewis acids are $B(C_6F_5)_3$, $AlCl_3$, and $AlBr_3$. Additionally, these Lewis acids can be used in combination. The total amount of the Lewis acid component used in the catalyst system is not particularly limited. However, to obtain liquid polymers, the Lewis acid component should be used in substantial molar excess relative to the alkyl magnesium component. Typically, the Lewis acid component should be used in an amount of from about 2 to about 50 moles per mole of alkyl magnesium component. Preferably, the Lewis acid should be used in an amount of from about 3 to about 10 moles per mole of alkyl magnesium component, and more preferably about 6 moles per mole of alkyl magnesium component.

Additionally, the catalyst system can contain other optional components known to those skilled in the art. One such group of compounds are promoters including acidic metal oxides (e.g., $Al_2O_3$, $ZrO_2$) and organic molecules with oxygen and nitrogen functionalities (e. g., $C_6F_5OH$).

The polymerization in accordance with this invention may be carried out at temperatures ranging from about 0° C. to about 200° C. Typically, however, the polymerization will be carried out at a temperature of from about 20° C. to about 80° C. The pressure at which the polymerization is carried out is not critical, with pressures ranging from 15 psi to 1500 psi being suitable. Typically, we used pressures ranging from 300 to 900 psi.

In another embodiment of the present invention, preferably at least one component of the catalyst system is supported by an inert support. Such inert supports are well known to those skilled in the art such as, for example, silica, alumina, carbon, zirconia, magnesia, diatomatious earth, kieselgur, and mixtures thereof. Supporting the components of the catalyst system to such inert support is accomplished by techniques well known to those skilled in the art such as, for example, impregnation.

The following examples further illustrate additional objects, advantages, and novel features of the invention. It will become apparent to those skilled in the art, however, that such examples are not intended to limit the scope of the invention.

The following materials were used in the examples given below. $Np_2Mg$ (Np=neopentyl) was prepared as described in the J. Org. Chem. 27, 1868, 1962 using neopentyl bromide, magnesium, and dioxane. A highly pure $Np_2Mg$ was obtained by sublimation of crude product twice at 100° C./60 mtorr. Diethylmagnesium was prepared from diethylmercury and magnesium as described in J. Organomet. Chem. 14, 1, 1968. Dibutylmagnesium, tris(pentafluorophenyl)boron ("FAB"), pentafluorophenol, aluminum chloride and bis(cyclopentadienyl)magnesium were all used as received from Aldrich. Chlorobenzene (from Aldrich) was dried over $LiAlH_4$ or $K_2CO_3$, and toluene (from Aldrich) was dried over Na benzophenone ketyl. Both solvents were stored under argon atmosphere with 4-Å molecular sieves. The reaction mixtures were prepared in a dry nitrogen-filled glove box. Polymerization reactions were performed in glass-lined 125 ml or stirred 300 ml autoclave manufactured by Parr Instrument Company.

EXAMPLE 1A

To a 50 ml glass liner equipped with a magnetic stirrer containing 40.8 mg (80 µmol) of tris(pentafluorophenyl)boron ("FAB") in 15 ml of chlorobenzene, 80 µmol (1.0 M heptane solution) of $Mg(C_4H_9)_2$ was added. The liner was put into a 125 ml Parr reactor. The reactor was filled and degassed with ethylene once and then pressurized with 700 psi of ethylene. After stirring at 60° C. for 1 hr, the unreacted ethylene was released and the reaction mixture containing a white solid was poured into 100 ml of methanol. The white solid was stirred for 5 hr in the methanol then filtered and washed with 40 ml of methanol. Finally, the product was dried under vacuum for 8 hr to yield 1.00 g of polyethylene. The $^1H$ NMR and $^{13}C$ NMR spectra of the polyethylene showed a singlet peak at 1.31 and 29.4 ppm, respectively, in 1,1,2,2-tetrachloroethane-$d_2$ at 130° C. The DSC of this polyethylene showed a melting point at 137° C. These results demonstrate the formation of a linear polyethylene.

EXAMPLE 1B–1K

Examples 1B through 1J followed the basic procedure for Example 1A above, except that ethylene was added in a single charge at 700 psi and FAB was added at 1 molar equivalent. The alkyl group on the dialkyl magnesium was either butyl, ethyl, or neopentyl and the solvent was either chlorobenzene or toluene. The amount of alkyl magnesium varied from 20 to 200 µmol and the amount of solvent used was either 15 or 50 ml. The reaction time varied from 0.5 to 4.0 hours and the reaction temperature was either room temperature or 60° C. The reaction conditions for all of the experiments in Example 1 are reported in Table 1. Table 1 also gives the results including the yield of solid polymer in grams and the reaction productivity.

TABLE 1

Conditions and Results for Example 1-$MgR_2$ + FAB → Solid Polymer

| Ex. | $MgR_2$ (µmol) | SOLVENT (ML) | TIME | TEMP | YIELD (G) | PRODUCTIVITY (kg/mol · hr) | M.W. (×10$^{-6}$) |
|---|---|---|---|---|---|---|---|
| 1A | $Mg(C_4H_9)_2$ (80) | $C_6H_5Cl$ (15) | 1.0 hr | 60° C. | 1.00 | 12.5 | 2.4 |
| 1B | $Mg(C_4H_9)_2$ (200) | $C_6H_5Cl$ (50) | 3.0 hr | r.t. | 10.5 | 17.5 | |
| 1C | $Mg(C_4H_9)_2$ (80) | $C_6H_5Cl$ (50) | 0.5 hr | 60° C. | 4.48 | 112.0 | |
| 1D | $Mg(C_4H_9)_2$ (20) | $C_6H_5Cl$ (15) | 4.0 hr | 60° C. | 1.55 | 19.4 | |
| 1E | $Mg(C_4H_9)_2$ (20) | $C_6H_5Cl$ (15) | 1.0 hr | 60° C. | 0.78 | 38.0 | |
| 1F | $Mg(C_4H_9)_2$ (100) | toluene (15) | 2.5 hr | 60° C. | 2.77 | 11.1 | |
| 1G | $Mg(C_4H_9)_2$ (80) | toluene (15) | 1.5 hr | 60° C. | 1.86 | 15.5 | 1.5 |
| 1H | $Mg(C_4H_9)_2$ (80) | toluene (15) | 1.0 hr | r.t. | 0.93 | 11.6 | |
| 1I | $Mg(Np)_2$ (60) | $C_6H_5Cl$ (15) | 0.5 hr | r.t. | 0.51 | 16.7 | |
| 1J | $Mg(Np)_2$ (90.2) | toluene (15) | 2.0 hr | 60° C. | 1.30 | 7.20 | |
| 1K | $Mg(C_2H_5)_2$ (80) | $C_6H_5Cl$ (15) | 1.0 hr | 60° C. | 0.40 | 5.00 | |

EXAMPLES 2A and 2B

These examples illustrate the addition of $C_6F_5OH$ to the reaction. To a 50 ml glass liner containing 15 ml of chlorobenzene and 200 µmol (1.0 M heptane solution) of $Mg(C_4H_9)_2$, 36.8 mg (200 µmol) of $C_6F_5OH$ was added. A colorless solid was immediately precipitated out of the solution. To the reaction mixture, 102.4 mg (200 µmol) of FAB was then added. The liner was placed in 125 ml of a Parr reactor. The reactor was filled and degassed with ethylene once then pressurized with 700 psi of ethylene. After stirring at 60° C. for 2 hr (5 hr for ex. 2B) the resulting polyethylene was treated as in example 1. Example 2A yielded 1.27 g and had a reaction productivity of 15.5 kg/mol·hr. Example 2B yielded 2.50 g and had a reaction productivity of 11.1 kg/mol·hr. Examples 2A and 2B are summarized in Table 2. These examples illustrate the use of an organic promoter.

TABLE 2

Conditions and Results for Example 2 - $MgR_2$ + $C_6F_5OH$ + FAB → Solid Polymer

| Example | $MgR_2$ (µmol) | Time | Temp. | Yield | Productivity |
|---|---|---|---|---|---|
| 2A | $Mg(C_4H_9)_2$ (200) | 2.0 hr | 60° C. | 1.27 g | 15.5 (kg/mol · hr) |
| 2B | $Mg(C_4H_9)_2$ (200) | 5.0 hr | 60° C. | 2.50 g | 11.1 (kg/mol · hr) |

EXAMPLES 3A and 3B

These examples demonstrate the use of the Lewis acid $AlCl_3$ instead of FAB. To a 50 ml glass liner equipped with a magnetic stirrer containing 10.8 mg (80 μmol) of AlCl₃ in 15 ml of chlorobenzene, 80 μmol (1.0 M heptane solution) of Mg(C₄H₉)₂ was added. The liner was placed in a 125 ml Parr reactor. The reaction mixture was stirred under N₂ for 20 min without ethylene. The reactor was filled and degassed with ethylene once and then pressurized with 700 psi of ethylene. After stirring at 60° C. for 1 hr, the resulting polyethylene was treated as in example 1 to yield solid polyethylene. Example 3A yielded 1.15 g and had a reaction productivity of 14.4 kg/mol·hr. Example 3B yielded 1.56 g and had a reaction productivity of 15.6 kg/mol·hr. Examples 3A and 3B are summarized in Table 3.

TABLE 3

Conditions and Results for Example 3 - MgR₂ + AlCl₃ (1 equiv.) → Solid Polymer

| Example | MgR₂ (μmol) | Time | Temp. | Yield | Productivity |
|---|---|---|---|---|---|
| 3A | Mg(C₄H₉)₂ (80) | 1.0 hr | 60° C. | 1.15 g | 14.4 (kg/mol · hr) |
| 3B | Mg(C₄H₉)₂ (200) | 0.5 hr | 60° C. | 1.56 g | 15.6 (kg/mol · hr) |

NMR and $^{13}$C NMR spectra (CDCl₃) of the product showed the formation of a hyperbranched polyethylene. The formation of a small amount of aryl-capped hyperbranched polymers via Friedel-Crafts reaction was also detected in this reaction.

EXAMPLES 4B–4H

Examples 4B through 4H followed the basic procedure for Example 4A above. All examples used 700 psi of ethylene in a single charge; the solvent used was 15 ml C₆H₅Cl and the reaction time was 1 hr. The MgR₂, reaction temperature, and equivalents of AlCl₃ was varied as given in Table 4. Table 4 also gives the results in terms of product yield, reaction productivity, molecular weight, Poly Dispersity Index (PDI), and branching index where the branching index (Me/Total) is defined as the ratio of methyl protons (at 0.85 ppm)/total alkyl protons (by $^{1}$H-NMR integration). In Table 4, Cp is "cyclopentadienyl". These examples illustrate the use of a range of temperatures and different amounts of Lewis acid.

TABLE 4

Conditions and Results for Examples 4A-4H-MgR₂ + AlCl₃ (>1 equiv.) → Branched Liquid Polymer

| Ex | MgR₂ (μmol) | TEMP | ALCL₃ | YIELD | Productivity (kg/mol · hr) | M.W. (>10⁻³) | PDI | Me/Total |
|---|---|---|---|---|---|---|---|---|
| 4A | Mg(C₄H₉)₂ (80) | 60° C. | 6 eq. | 3.30 g | 41.3 | 4.6 | 1.33 | 0.33 |
| 4B | Mg(C₄H₉)₂ (80) | 60° C. | 3 eq. | 0.50 g | 6.3 | 1.3 | 2.36 | 0.44 |
| 4C | Mg(C₄H₉)₂ (80) | 60° C. | 10 eq. | 3.85 g | 48.1 | 4.0 | 1.34 | 0.32 |
| 4D | Mg(Cp)₂ (80) | 60° C. | 3 eq. | 1.90 g | 23.8 | 3.4 | 1.63 | 0.43 |
| 4E | Mg(Cp)₂ (80) | 60° C. | 6 eq. | Trace | | | | |
| 4F | Mg(C₄H₉)₂ (80) | r.t. | 6 eq. | 1.08 g | 13.5 | 2.3 | 1.38 | 0.39 |
| 4G | Mg(C₄H₉)₂ (80) | 100° C. | 6 eq. | 3.59 g | 44.9 | 2.8 | 2.36 | 0.34 |
| 4H | Mg(C₄H₉)₂ (80) | 150° C. | 6 eq | 4.53 g | 56.6 | 0.5 | 2.56 | 0.46 |

EXAMPLE 4A

This example demonstrates the production of highly branched viscous liquid polyethylene especially useful in lubricant applications. To a 50 ml glass liner equipped with a magnetic stirrer containing 64.8 mg (480 μmol) of AlCl₃ in 15 ml of chlorobenzene, 80 μmol (1.0 M heptane solution) of Mg(C₄H₉)₂ was added. The liner was placed in 125 ml Parr reactor. The reaction mixture was stirred under N₂ for 20 min without ethylene at 60° C. The reactor was filled and degassed with ethylene once and then pressurized with 700 psi of ethylene. After stirring at 60° C. for 1 hr, the resulting reaction mixture was poured into 20 ml of pentane. The mixture was filtered and the solution was dried under vacuum at 60° C. to yield 3.30 g of a viscous oil. The $^{1}$H

EXAMPLES 4I–4L

Examples 4I through 4L followed the basic procedure for Example 4A above. All examples used: a constant feed of ethylene; 6 equivalents of AlCl₁₃; 15 ml of C₆H₅Cl; a reaction temperature of 60° C.; and a reaction time of 1 hr. The amount of ethylene charge was varied from 300 psi to 900 psi as given in Table 5. Table 5 also gives the results in terms of product yield, reaction productivity, molecular weight, PDI, and branching index where the branching index (Me/Total) is defined as the ratio of methyl protons (at 0.85 ppm)/total alkyl protons (by $^{1}$H-NMR integration). These examples indicates an increase in reaction productivity with increasing ethylene pressure.

TABLE 5

Conditions and Results for Examples 4I–4L-MgR$_2$ + AlCl$_3$ (>1 equiv.) → Branched Liquid Polymer

| Ex | MgR$_2$ (μmol) | Ethylene (psi) | ALCL$_3$ | YIELD | Productivity (kg/mol · hr) | M.W. (×10$^{-3}$) | PDI | Me/Total |
|---|---|---|---|---|---|---|---|---|
| 4I | Mg(C$_4$H$_9$)$_2$ (80) | 900 | 6 eq. | 5.70 g | 71.3 | 2.3 | 1.73 | 0.37 |
| 4J | Mg(C$_4$H$_9$)$_2$ (80) | 700 | 6 eq. | 5.62 g | 70.3 | 1.9 | 1.70 | 0.38 |
| 4K | Mg(C$_4$H$_9$)$_2$ (80) | 500 | 6 eq. | 5.30 g | 66.3 | 2.7 | 2.81 | 0.39 |
| 4L | Mg(C$_4$H$_9$)$_2$ (80) | 300 | 6 eq. | 3.43 g | 42.9 | 2.2 | 1.74 | 0.36 |

Although the invention has been described in detail in the foregoing embodiments for the purpose of illustration, it is to be understood that such detail is solely for that purpose and that variations can be made therein by those skilled in the art without departing from the spirit and scope of the invention except as it may be limited by the claims.

What is claimed is:

1. A catalyst system for catalyzing the oligomerization or polymerization of ethylene to homopolymers consisting essentially of:
   (a) a magnesium containing component having the formula MgR$_2$ wherein R is a hydrocarbyl group; and
   (b) a Lewis acid component.

2. The catalyst system of claim 1 wherein R is selected from the group consisting of methyl, ethyl, propyl, isopropyl, butyl, isobutyl, pentyl, cyclopentyl, cyclohexyl, and fluorinated alkyls and aryls.

3. The catalyst system of claim 1 wherein said magnesium containing component is selected from the group consisting of diethylmagnesium having the formula Mg(C$_2$H$_5$)$_2$, dibutylmagnesium having the formula Mg(C$_4$H$_9$)$_2$, and dineopentylmagnesium having the formula Mg(Np)$_2$.

4. The catalyst system of claim 1 wherein said Lewis acid component is selected from the group consisting of B(C$_6$F$_5$)$_3$, B(C$_6$H$_5$)$_3$, BF$_3$, AlR'$_n$X$_{3-n}$, PF$_5$, alkylaluminoxanes, and mixtures thereof, wherein R'=alkyl, X=C$_6$F$_5$, F, Cl, or Br and n=0–2.

5. The catalyst system of claim 1 wherein said Lewis acid component is selected from the group consisting of AlCl$_3$, AlBr$_3$, B(C$_6$F$_5$)$_3$ and mixtures thereof.

6. A catalyst system for catalyzing the oligomerization or polymerization of ethylene to homopolymers consisting essentially of:
   (a) a magnesium containing component selected from the group consisting of diethylmagnesium having the formula Mg(C$_2$H$_5$)$_2$, dibutylmagnesium having the formula Mg(C$_4$H$_9$)$_2$, and dineopentylmagnesium having the formula Mg(Np)$_2$; and
   (b) a Lewis acid component selected from the group consisting of AlCl$_3$, AlBr$_3$, B(C$_6$F$_5$)$_3$ and mixtures thereof.

7. A method of synthesizing homopolymers or copolymers of ethylene comprising contacting under polymerization conditions:
   (a) ethylene; and
   (b) a catalyst system consisting essentially of:
      (i) a magnesium containing component having the formula MgR$_2$ wherein R is a hydrocarbyl group; and
      (ii) a Lewis acid component.

8. The method of claim 7 wherein the reaction takes place in the presence of a halogenated or non-halogenated hydrocarbon solvent.

9. The method of claim 7 wherein R in said magnesium containing component of the catalyst system is selected from the group consisting of methyl, ethyl, propyl, isopropyl, butyl, isobutyl, pentyl, cyclopentyl, cyclohexyl, and fluorinated alkyls and aryls; and wherein said Lewis acid component is selected from the group consisting of B(C$_6$F$_5$)$_3$, B(C$_6$H$_5$)$_3$, BF$_3$, AlR'$_n$X$_{3-n}$, PF$_5$, alkylaluminoxanes, and mixtures thereof, wherein R' is alkyl, X is selected from the group consisting of C$_6$F$_5$, F, Cl, and Br, and n equals 0, 1 or 2.

10. The method of claim 7 wherein said magnesium containing component of the catalyst system is selected from the group consisting of diethylmagnesium having the formula Mg(C$_2$H$_5$)$_2$, dibutylmagnesium having the formula Mg(C$_4$H$_9$)$_2$, and dineopentylmagnesium having the formula Mg(Np)$_2$; and wherein the Lewis acid component is selected from the group consisting of AlCl$_3$, AlBr$_3$, B(C$_6$F$_5$)$_3$ and mixtures thereof.

11. The method of claim 10 wherein the reaction takes place in the presence of a halogenated or non-halogenated solvent.

12. A method of synthesizing a viscous, oily, hydrocarbon composition comprising contacting under polymerization conditions:
   (a) ethylene; and
   (b) a catalyst system consisting essentially of:
      (i) a magnesium containing component having the formula MgR$_2$ wherein R is a hydrocarbyl group; and
      (ii) a Lewis acid component, wherein said Lewis acid component is in an amount greater than one molar equivalent relative to the magnesium containing component,
said contacting being done in the presence of a halogenated or non-halogenated hydrocarbon solvent.

13. The method of claim 12 wherein the Lewis acid component is added in an amount greater than about 3 molar equivalents to the magnesium containing component.

14. A hydrocarbon composition produced by the process of claim 7.

15. A viscous, oily, hydrocarbon composition produced by the process of claim 12 and having a molecular weight in the range of about 300 to about 30,000.

16. A synthetic lubricant basestock comprising the hydrocarbon composition of claim 15.

17. The composition of claim 15 further comprising lubricating oil additives selected from the group consisting of antioxidants, anti-wear additives, extreme pressure antioxidants, anti-wear additives, high pressure additives, friction modifiers, viscosity index improvers, pour point depressants, detergents, dispersants, corrosion inhibitors, metal deactivators, seal compatibility additives, demulsifiers, anti-foam additives, and mixtures thereof.

* * * * *